United States Patent [19]
Wang

[11] Patent Number: 5,503,168
[45] Date of Patent: Apr. 2, 1996

[54] DENTAL FLOSS DEVICE

[75] Inventor: Gang Wang, Cypress, Calif.

[73] Assignee: Nupro, Inc., San Diego, Calif.

[21] Appl. No.: 337,102

[22] Filed: Nov. 10, 1994

[51] Int. Cl.⁶ .................................................. A61C 15/00
[52] U.S. Cl. ............................................ 132/324; 132/323
[58] Field of Search ................................. 132/321, 323, 132/324, 325; D28/64

[56]    References Cited

U.S. PATENT DOCUMENTS

| | | | |
|---|---|---|---|
| 3,696,821 | 10/1972 | Adams | 132/91 |
| 4,727,895 | 3/1988 | Berarducci | 132/91 |
| 4,852,728 | 8/1989 | Court | 206/63.5 |
| 5,199,452 | 4/1993 | Cheng | 132/325 |

Primary Examiner—John G. Weiss

[57]    ABSTRACT

A dental floss device for relieving the fingers from being tightly wound with floss and being in contact with wet and soiled spent floss comprises two sleeves—a take-up sleeve for receiving spent floss and a supply sleeve for containing pre-wound fresh floss and an end plug as a cover for the supply sleeve. The use of the device allows a strand of floss to be wound around the take-up sleeve and the end plug respectively instead of directly around fingers while flossing with the device is much the same as flossing with bare hands—a way of flossing which millions are used to. Further, the device is self-contained and reusable. When the supply of fresh floss on the supply sleeve is exhausted, a new pre-wound supply sleeve can be used to replace the exhausted one.

9 Claims, 2 Drawing Sheets

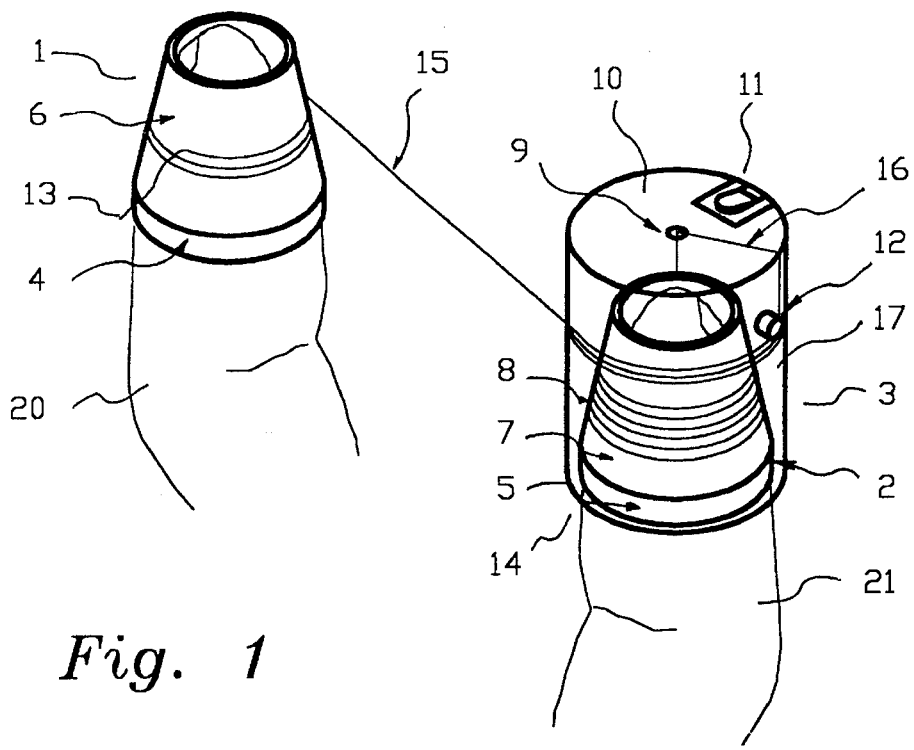
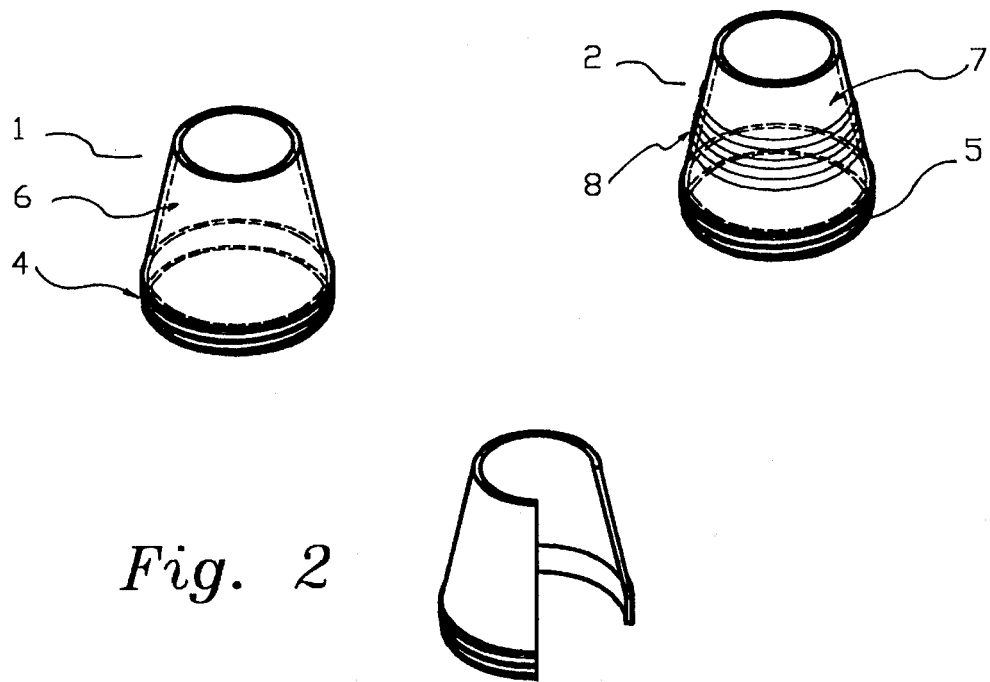
Fig. 1
Fig. 2

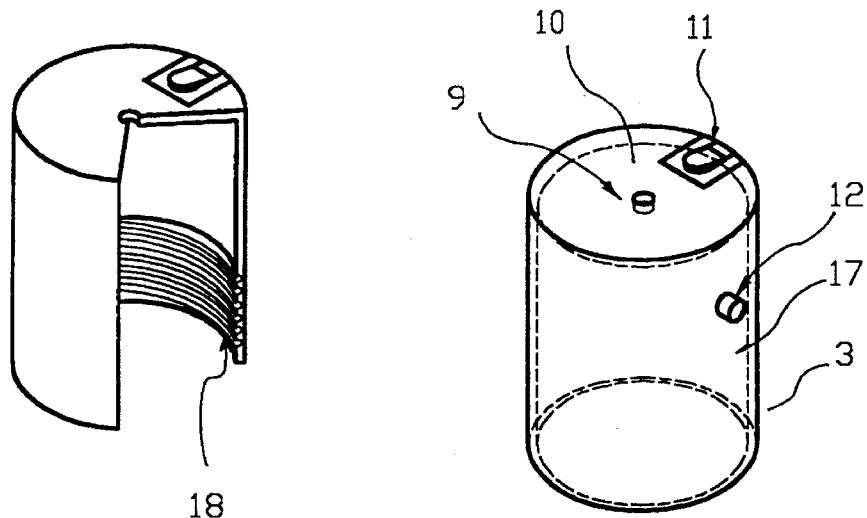
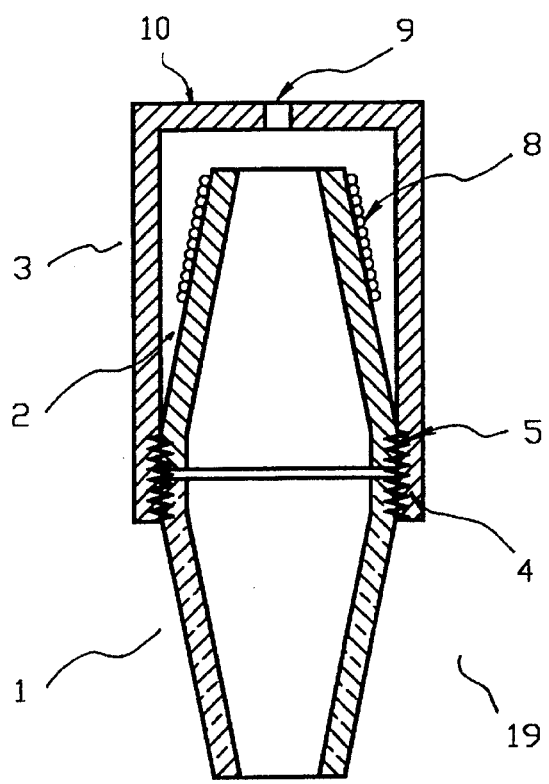
Fig. 3
Fig. 4

DENTAL FLOSS DEVICE

BACKGROUND OF THE INVENTION

1. Field of the Invention

This invention relates in general to a dental floss device, and in particular to a self-contained and reusable dental floss device that is easy to operate and inexpensive to manufacture.

2. Prior Art

Flossing teeth regularly has long been recommended by dentists and is practiced by many people around the world. The conventional way of flossing is wrapping the free ends of a strand of dental floss around middle fingers of each hand. The floss section between the fingers is kept tensioned and guided by index fingers and thumbs and then passed successively between tooth pairs. The tensioning makes it necessary for the floss to be wrapped around middle fingers very tightly to prevent the floss from slipping. In addition, fresh floss has to be fed from one of the fingers to replace soiled/frayed section which in turn is wound onto the other finger. Anyone who has flossed knows that tightly wrapped fingers are not very comfortable. Often times the wrapped fingers turn to purple and feel numb due to lack of blood flow. Further, one of the holding fingers is wrapped by spent floss which is wet and soiled causing additional discomfort for the user.

Dental floss devices/holders/applicators have been invented in attempt to make dental flossing easier and less painful. A search revealed numerous United States Patents issued concerning dental flossing devices/holders/applicators. The following US Patents are believed to be more closely related to the current invention:

| 553,610   | 4,051,857 | 5,056,540 |
|-----------|-----------|-----------|
| 1,306,998 | 4,094,328 | 5,060,681 |
| 1,640,607 | 4,460,002 | 5,067,503 |
| 2,187,442 | 4,706,694 | 5,069,233 |
| 3,746,017 | 4,790,336 | 5,105,840 |
| 3,927,687 | 4,807,651 | 5,125,424 |

All the dental floss devices described in the prior art, regardless of their appearance and complexity in structure, include a handle and a floss head where a tensioned string member is held. Users of these devices floss by holding on to the handle and extending the floss head into the mouth and passing the tensioned string member between tooth pairs. Most of these devices have the floss head fixed in position. Others such as The Dimitroff U.S. Pat. No. 1,306,998, The Ray U.S. Pat. No. 4,094,328 and The Lamber U.S. Pat. No. 4,706,694 offer some limited degree of flexibility by allowing the floss head to rotate relative to the handle. However, teeth are oriented in various directions and complex ways. Some of them like front ones are straight forward while those in the back are often hard and awkward to reach. Proper and effective flossing requires complex manipulation of floss including continuous change in direction, tension and motion of floss string between tooth pairs and around teeth inside mouth. Such maneuvering is not an easy chore for even highly flexible human hands and certainly a very difficult task for floss devices with no or limited flexibility. Therefore, whatever the merits, features and advantages of the devices disclosed in the prior art, none of them can provide as adequate means for proper and effective flossing as human hands can.

In addition, in considering their structure and functioning, all the devices described in the prior art can be categorized as disposable and reusable. Devices of the disposable type are usually simple in structure and inexpensive to use. However, one such device can hardly last long. Once the tensioned string member becomes frayed, it can no longer be used effectively. As a result, a user usually needs several of these disposable devices to complete full mouth flossing. As inexpensive as these devices may seem, the accumulated cost can still be substantial. And so is the impact on environment as these devices are usually made of non-degradable materials such as plastic. On the other hand, the devices of the reusable type usually last long time with only floss cartridges needed to be replaced intermittently. Nevertheless, they are inherently much more complicated in structure—providing tension and dispensing of floss are accomplished by mechanical means involving many parts which increase the complexity of the devices as well as the cost to manufacture and to use.

The dental floss device disclosed in the current invention takes full advantage of the flexibility and maneuverability of human hands as well as the habit of flossing with bare hands which millions of people have developed. Among other features and advantages, the most distinctive feature of the dental floss device disclosed in the current invention is that the device relieves fingers from being wrapped tightly and being in contact with wet and soiled spent floss while flossing with the device is very much the same as flossing with bare hands. Moreover, this device is self-contained, reusable and is easier and less expensive to manufacture.

SUMMARY OF THE INVENTION

It is a principal object of the present invention to provide a device for use in daily dental flossing which relieves the fingers from being tightly wrapped with floss and being in contact with wet and soiled spent floss while flossing with the device is in much the same way as flossing with bare hands.

It is also an object of the present invention to provide a self-contained and reusable floss device which is easier and less expensive to manufacture.

The foregoing objects can be accomplished by providing a dental floss device having two sleeves—a take-up sleeve for receiving spent floss and a supply sleeve for containing fresh floss, and one cylindrical end plug as a cover for the supply sleeve. The supply sleeve is pre-wound with fresh floss and is detatchably plugged into the end plug to keep pre-wound floss covered for sanitation reasons and to form a supply sleeve-plug assembly. A small hole is drilled at the center of the plugged end of the end plug to allow the fresh floss to pass through and to be retrieved from the supply sleeve when the supply sleeve is covered by the end plug.

When flossing with the floss device described above, one, depending on one's flossing habit, sticks the middle or index fingers of each hand into the take-up sleeve and the supply sleeve-plug assembly respectively. The free end of a strand of fresh dental floss from the pre-wound supply sleeve passing through the hole on the end plug is tightly wound around the circumferential surface of the take-up sleeve while the continuous end of the floss is wrapped around the circumferential surface of the end plug tightly. As such, the floss is wrapped around the take-up sleeve and the end plug of the supply sleeve-plug assembly instead of directly around the fingers, thus avoiding the discomfort caused by tightly wrapped floss around the fingers. Flossing with the device thereafter is just like flossing with bare hands. The tightly held floss is guided and assisted by index or middle fingers and thumbs to pass successively between tooth pairs inside mouth. Dispensing floss is performed by winding the spent floss towards and onto the take-up sleeve and unwinding fresh floss from the supply sleeve-plug assembly. The wet and soiled spent floss is thus wound around the take-up sleeve instead of directly around the finger. Therefore, flossing with this device as described above is much the same as flossing with bare hands which millions are familiar with except that fingers suffer less.

After flossing, the spent floss can be cut with a cutting device attached to the end plug and the take-up sleeve can be cleaned while fresh floss can be retrieved from the supply sleeve in preparation for next use. Further, the detachable arrangement of the supply sleeve with the end plug allows for easy replacement of an exhausted supply sleeve with a new and pre-loaded supply sleeve, thus making the device self-contained and reusable. Finally, as the supply sleeve is preferably identical to the take-up sleeve, an empty supply sleeve can be used to replace a used take-up sleeve for sanitation reasons.

BRIEF DESCRIPTION OF THE DRAWINGS

FIG. 1 is a top perspective of a dental floss device in accordance with the present invention, threads on take-up sleeve, supply sleeve and end plug are omitted so that the figure can be viewed more clearly;

FIG. 2 is a top perspective of the take-up and supply sleeves of such device along with a perspective view partially in section;

FIG. 3 is a top perspective of the end plug of such device along with a perspective view partially in section; and FIG. 4 is a side elevation in section of such device when both supply sleeve and take-up sleeve are screw-in attached to the end plug.

DETAILED DESCRIPTION

Refer now to FIG. 1, which is an overall drawing of a preferred embodiment in accordance with the present invention. The dental floss device has a take-up sleeve 1 for jacketing a finger 20 and for receiving spent floss which is wound around take-up sleeve 1, a supply sleeve 2 for jacketing another finger 21 and for containing pre-wound fresh floss 8, and an end plug 3 as a cover for supply sleeve 2 around which another end of floss is to be wound, all made of rigid, light weight, non-toxic and inexpensive material.

As shown in FIG. 2, sleeves 1 and 2 are preferably identical with generally uniform wall thickness and of the shape of frustum of a cone with a short straight threaded section 4 and 5 at the end of larger diameter. As the thickness of fingers are generally uniform with a slight and gradual decrease towards finger tips, the configuration of sleeves 1 and 2 renders easy conformation of fingers of different sizes to the shape of bore of sleeves 1 and 2 for tight grip. Further, the inside surface of sleeves 1 and 2 is made coarse and rough for additional grip between the sleeves and fingers which are stuck tightly into the bore of sleeves 1 and 2 during flossing. The outside or circumferential surface of the tapered portion 6 and 7 of sleeves 1 and 2 are also coarse and rough so as to deter slip between the surfaces and floss wrapped around them. And a supply of fresh floss 8 is pre-wound around the tapered portion 7 of supply sleeve 2 to a diameter smaller than the diameter of the larger end of the frustum so that end plug 3 can envelop the pre-wound supply sleeve without its inside surface touching the pre-wound floss.

As shown in FIG. 3, the circumferential surface 17 of cylindrical end plug 3 is also coarse and rough for deterring slip between the surface and floss wrapped around it. At the center of plugged end 10 of the end plug 3 is a hole 9 for allowing floss 8 to pass through and to be retrieved from supply sleeve 2 which is covered by end plug 3. Hole 9 is large enough so that floss can be lead through easily without tools, yet small enough so that pre-wound fresh floss 8 is well covered. Also on top of the plugged end 10 is a cutting device 11 suitable for cutting floss which is similar to that attached to the regular floss dispensers available in market. Additionally, a short stud 12 is attached on circumferential surface 17 for redirecting fresh floss coming out from hole 9 in axial direction of end plug 3 to the transverse direction of end plug 3 so that the floss can be securely and tightly wound around end plug 3 as illustrated in FIG. 1. Moreover, as shown in FIG. 3, along the inside of the open end of end plug 3 is a portion 18 threaded to match threads 4 and 5 of take-up sleeve 1 and supply sleeve 2 so that both sleeves 1 and 2 can be screw-in attached to end plug 3 such as illustrated in FIG. 4.

In use as shown in FIG. 1, supply sleeve 2 is plugged into end plug 3 to cover pre-wound floss 8 in a screw-in manner and to form a supply sleeve-plug assembly 14 while a section of floss 15 of proper length is retrieved from supply sleeve 2 through hole 9 on end plug 3. To prepare for flossing, one sticks middle fingers 20 and 21 of both hands into the bore of take-up sleeve 1 and supply sleeve 2 until the finger tips are tightly and securely gripped. Free end 13 of floss section 15 is then wound around take-up sleeve 1 tightly. As tension is required during flossing, the continuous end 16 of floss 15 has to be secured otherwise fresh floss will be pulled out of supply sleeve 2 whenever tension is applied to the floss. This is accomplished by directing floss 15 around stud 12 and then wrapping around the end plug 3 transversely until the section of floss across take-up sleeve 1 and supply sleeve-plug assembly 14 is of suitable length for flossing. Since the circumferential surfaces of both take-up sleeve 1 and end plug 3 are coarse and rough, the friction between the surfaces and floss wrapped around them help secure the floss and prevent slip. The tensioned floss 15 is then guided by index fingers and thumbs to pass through tooth pairs successively. When the floss is frayed and soiled, it is wound toward and around take-up sleeve 1 and fresh floss is unwound from end plug 3 to replace the spent floss section.

After flossing, the spent floss wound around take-up sleeve 1 can be cut with cutting device 11 from fresh floss contained inside end plug 3. And take-up sleeve 1 can then be cleaned for sanitation reasons while, in preparation for next use, a section of fresh floss can be retrieved from supply sleeve 2. In addition, detachable arrangement between supply sleeve 2 and end plug 3 allows for easy replacement of an exhausted supply sleeve with a new and pre-wound supply sleeve which can be supplied separately, thus making the device self-contained and reusable. Further, as take-up sleeve 1 and supply sleeve 2 are preferably identical thus interchangeable, an exhausted supply sleeve can be used to replace a used take-up sleeve for sanitation reasons. Finally, to make the device compact and convenient to carry, take-up sleeve 1 can be backward screw-in attached onto end plug 3 at the end of supply sleeve 2 as shown in FIG. 4 to form a single piece 19.

A dental floss device described above relieves fingers from being tightly wrapped with floss and being contact with wet and soiled spent floss while flossing with the device is much the same as flossing with bare hands. The device is also simple in structure; the sleeves 1 and 2 and cylindrical end plug 3 are simple in shape and can easily be manufactured by manufacturing process such as plastic injection molding. Consequently, the device in accordance with the present invention is easy and inexpensive to manufacture.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A self-contained and reusable dental flossing device for relieving fingers from being tightly wrapped by floss and in direct contact with the soiled spent floss during flossing, said flossing device comprising:

a supply sleeve with an opening and shape to permit the covering of a finger tip of a user, said supply sleeve having an outer surface with a supply of fresh flossing material wound around said outer surface, an end plug having a generally cylindrical body and having an open lower end extending over said supply sleeve to cover said fresh flossing material on said supply sleeve, said end plug having a floss supply hole on a closed upper end through which a strand of said flossing material is passed, said strand of flossing material having a free end and a continuous end extending from said fresh flossing material on said supply sleeve through said floss supply hole, said end plug having an outer surface around which portion of said strand of flossing material near said continuous end is tightly wound, a take-up sleeve with an opening and shape to permit the covering of a finger tip of a user, said take-up sleeve having an outer surface around which said free end of flossing material is tightly wound so as to allow a section of said strand of fresh flossing material extending from said floss supply hole to be held in tension between said end plug and said take-up sleeve during flossing by the user.

2. The dental flossing device of claim 1, wherein said sleeves are identical and have a frustum shape with a lower cylindrical threaded section.

3. The dental flossing device of claim 1, wherein an inner surface of said end plug is threaded to be removably connected to said threaded section of said supply sleeve for easy replacement of an exhausted supply sleeve with a pre-wound supply sleeve.

4. The dental flossing device of claim 1, wherein the inside surface of each sleeve is rough for additional frictional grip between said sleeves and the finger tips of the user.

5. The dental flossing device of claim 1, wherein said outer surfaces of said sleeves and said end plug are rough to deter slippage between said surfaces and said flossing material wound around said outer surfaces.

6. The dental flossing device of claim 1, wherein said outer surface of said end plug has a short stud thereon to redirect the direction of said flossing material that extends from said floss supply hole from an axial direction of said end plug to a transverse direction of said outer surface of said end plug such that said flossing material can be easily wound around said outer surface of said end plug in the transverse direction of said end plug.

7. The dental flossing device of claim 1, wherein said end plug has a cutting device on the closed end to permit the cutting of the spent flossing material from said fresh flossing material.

8. A self-contained and reusable dental flossing device for relieving fingers from being tightly wrapped by floss and in direct contact with the soiled spent flossing material, said flossing device comprising:

a supply sleeve having an opening and shape to permit the covering of a finger tip of a user, said supply sleeve having an outer surface around which a supply of fresh flossing material is wound, a cylindrical end plug having an open lower end extending over said supply sleeve to cover said fresh flossing material on said supply sleeve, said end plug having a floss supply hole on a closed upper end through which a strand of said flossing material is passed, said strand of flossing material having a free end and a continuous end extending from said fresh flossing material on said supply sleeve through said floss supply hole, said end plug having an outer surface around which portion of said strand of flossing material near said continuous end is tightly wound, said end plug having a cutting device to permit cutting of the spent flossing material from the fresh flossing material, a take-up sleeve having an opening and shape to permit the covering of a finger tip of a user, said take-up sleeve being adapted to receive said free end of said flossing material so as to allow a section of said flossing material extending from said floss supply hole to be held in tension between said end plug and said take-up sleeve during flossing by the user.

9. A self-contained and reusable dental flossing device for relieving fingers from being tightly wrapped by floss and in direct contact with the soiled spent flossing material, said flossing device comprising:

a supply sleeve with an opening and shape to permit the covering of a finger tip of a user, said supply sleeve having an outer surface with a supply of fresh flossing material wound around said outer surface, an end plug having an open lower end extending over said supply sleeve to cover said fresh flossing material on said supply sleeve, said end plug having a floss supply hole on a closed upper end through which a strand of said flossing material is passed, said strand of flossing material having a free end and a continuous end extending from said fresh flossing material on said supply sleeve through said floss supply hole, said end plug having an outer surface around which portion of said strand of flossing material near said continuous end is tightly wound, a take-up sleeve with an opening and shape to permit the covering of a finger tip of a user, said free end of said flossing material being tightly wound around said take-up sleeve so as to allow a section of said flossing material extending from said floss supply hole to be held in tension between said end plug and said take-up sleeve during flossing by the user, said sleeves being identical and having a frustum shape with a lower cylindrical threaded section, an inner surface of said end plug threaded to be removable to said threaded section of said supply sleeve for easy replacement of an exhausted supply sleeve with a pre-wound supply sleeve, said inner surface of each sleeve being rough for additional grip between said sleeves and the finger tips of the user, the outer surfaces of said sleeves and said end plug being rough to deter slippage between said surfaces and said flossing material wound around said outer surfaces, said outer surface of said end plug having a short stud thereon to redirect the direction of said flossing material that extends from said floss supply hole from an axial direction of said end plug to a transverse direction of said outer surface of said end plug such that said flossing material can be easily wound around said outer surface of said end plug in the transverse direction of said end plug, and said end plug having a cutting device on the closed end to permit the cutting of the spent flossing material from the fresh flossing material.

* * * * *